United States Patent [19]

Candiani et al.

[11] Patent Number: 5,382,669
[45] Date of Patent: Jan. 17, 1995

[54] PROCESS FOR THE PREPARATION OF ERGOLINE DERIVATIVES

[75] Inventors: Ilaria Candiani, Busto Arsizio; Walter Cabri, Rozzano; Angelo Bedeschi, Milan; Franco Zarini, Settimo Milanese, all of Italy

[73] Assignee: Farmitalia Carlo Erba S.R.L., Milan, Italy

[21] Appl. No.: 28,286

[22] Filed: Mar. 9, 1993

[30] Foreign Application Priority Data

Mar. 12, 1992 [GB] United Kingdom ............... 9205439

[51] Int. Cl.$^6$ .............................. C07D 457/04
[52] U.S. Cl. ................................................ 546/69
[58] Field of Search ........................................ 546/69

[56] References Cited

FOREIGN PATENT DOCUMENTS 2103603 2/1983 United Kingdom .

Primary Examiner—Johann Richter
Assistant Examiner—Catherine S. Kilby Scalzo
Attorney, Agent, or Firm—Oblon, Spivak, McClelland, Maier & Neustadt

[57] ABSTRACT

The invention provides a process for the preparation of ergoline derivatives of the formula I

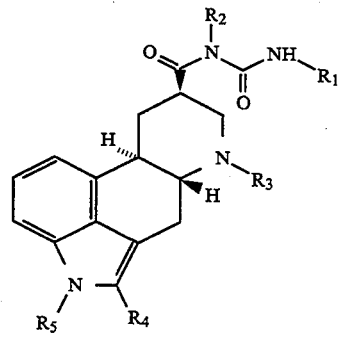

the process comprising reacting an ergoline amide of the formula II with an isocyanate of formula III

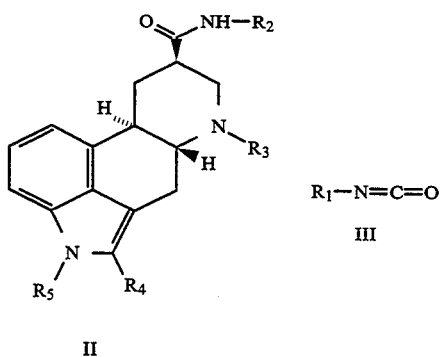

in presence of a metal catalyst and of a phosphorus compound. The compounds of the formula I are useful antiprolactinic and antiparkinson agents.

18 Claims, No Drawings

PROCESS FOR THE PREPARATION OF ERGOLINE DERIVATIVES

The invention relates to a process for the preparation of ergoline derivatives.

The invention provides a process for the preparation of ergoline derivatives of the formula I

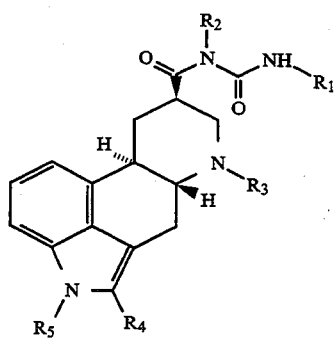

I wherein $R_1$ represents an alkyl group having from 1 to 4 carbon atoms, a cyclohexyl group or a phenyl group or a dimethylamino alkyl group $(CH_2)_nN(CH_3)_2$ in which n is an integer, $R_2$ represents any of the group which $R_1$ may represent, or a hydrogen atom or a pyridyl, pyrimidyl, pyrazinyl, pyridazinyl, thiazolyl or thiadiazolyl residue, $R_3$ represents a hydrocarbon group having from 1 to 4 carbon atoms, $R_4$ represents a hydrogen or a halogen atom or a methylthio or phenylthio group and $R_5$ represents a hydrogen atom or a methyl group, the process comprising reacting an ergoline amide of the formula II with an isocyanate of formula III.

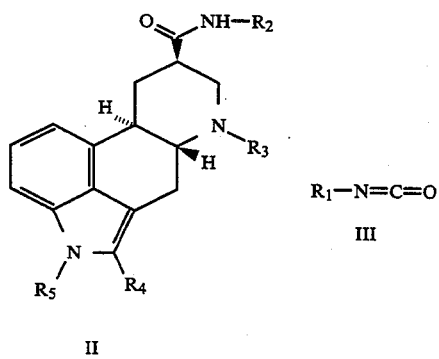

II $R_1$—N=C=O

III wherein $R_1$, $R_2$, $R_3$, $R_4$ and $R_5$ have the above given meanings, in presence of a metal catalyst and of a phosphorus compound. The reaction is typically performed in a suitable solvent at a temperature of from 0° to 80° C.

The compounds of the formula I are useful antiprolactinic and antiparkinson agents as described and claimed in our British Patent Specifications 2074566 and 2103603 which also disclose two processes for their preparation, one consisting of the reaction of the 8-carboxylergoline with a carbodiimide and the other ones characterized by the reaction of the ergoline amide with a very large excess of isocyanate (up to 36 equivalents) and at a temperature of from 70° to 120° C.

This latter process needs a large excess of compounds of the formula III for obtaining a good conversion (see *Eur. J. Med. Chem.*, 24, (1989), 421–426).

The use of isocyanates in large quantities has to be avoided in industrial processes owing to the dangerous properties and the toxicity of such reactants (N. Irving Sax *Dangerous properties of industrial materials*, 1968, Ed. Van Nostrand Reinhold; Schueler, D, *Farbe Lack* 1987, 93, 19–21, C.A. 106: 72102q; Mowe, G. *Contact dermatitis*, 1980, 6, 44–45, C.A. 93: 31108r; Davis, D. S.; DeWolf, G. B.; Nash, R. A.; Stelling, J. S. *Report*, 1989, DCN-87-203-068-05-05, EPA/600/8-87/034M, C.A. 113: 11426w).

Moreover, the use of phosphorus compounds surprisingly modulates the metal activation of isocyanate, thereby avoiding its addition to the indole nitrogen of the compounds of the formula II, when $R_5$ is a hydrogen atom.

The process of the present invention is much safer and may be carried out under milder conditions than the previous one, avoiding the use of large quantities of isocvanates; furthermore the products of formula I are obtained with higher selectivity.

Suitable metal catalysts include Ib and IIb metal group salts (for example $Zn^{11}$ or Ag salts) and preferably $Cu^I$ and $Cu^{II}$ salts. Most preferred are CuCl, $CuCl_2$, CuBr and CuI.

Suitable phosphorus compounds include $C_1$–$C_4$ alkyl, and optionally substituted $C_6$–$C_{10}$ aryl, such as phenyl or naphthyl phosphines of general formula $PR^6R^7R^8$ in which $R_6$, $R_7$ and $R_8$ can each, independently, be an alkyl or aryl group optionally substituted by one or more substituents chosen from Cl, F, methyl, methoxy; suitable phosphorus compounds can also be alkyl phosphites; preferred phosphorus compounds are triarylphosphine and more preferred triphenylphosphine and triparatolylphosphine. Suitable solvents are dichloromethane, 1,1-dichloroethane, chloroform, toluene, acetonitrile and dimethylformamide; preferred solvents are toluene, chloroform, dichloromethane and 1,1-dichloroethane; most preferred solvents are dichloromethane and dichloroetane.

The reaction is preferably carried out at a temperature from 35° to 60° C.

From 1 to 4 equivalents of the compound of formula III are used, and preferably from 2 to 3 equivalents.

The halogen atom which $R_4$ may represent is preferably a chlorine or bromine atom; nevertheless, it may be a fluorine atom. The hydrocarbon group which $R_3$ may represent may be an alkyl or cycloalkyl group or an ethylenically or acetylenically unsaturated group. Examples include methyl, ethyl, n-propyl, isopropyl, butyl, t-butyl, isobutyl, cyclopropyl, methylcyclopropyl, vinyl, allyl and propargyl groups.

Preferably $R_1$ is an alkyl group having from 1 to 4 carbon atoms or a cyclohexyl group; most preferred $R_1$ are linear alkyls having from 1 to 4 carbon atoms; preferred $R_2$ is a dimethylaminopalkyl group $(CH_2)_nN(CH_3)_2$ in which n=1, 2, 3 or 4; $R_3$ is preferably allyl and $R_4$ and $R_5$ are hydrogen atoms. The starting materials employed in the process according to the invention may be prepared by established procedures starting from known compounds, moreover some compounds of formula II are described in our European Patent Specification No 70562, in our Belgian Patent No 888243, in our German patent application No 3112861 and in our Japanese patent application No 81/48491.

The reaction product may be isolated and purified following conventional procedures, for example chromatography and/or crystallization and salt formation.

The ergoline derivatives of formula (I) can be converted into pharmaceutically acceptable salts. The ergoline derivatives of formula (I), or the pharmaceutically acceptable salts thereof, can be subsequently formulated with a pharmaceutically acceptable carrier or diluent to provide a pharmaceutical composition.

The following examples illustrate the invention.

EXAMPLE 1

6-Allyl-8β-[1-ethyl-3-(3-dimethylamminopropyl)-ureidocarbonyl]-ergoline (I: $R_1=C_2H_5$, $R_2=(CH_2)_3N(CH_3)_2$, $R_3=CH_2CHCH_2$)

5 g of 6-Allyl-8β-(3-dimethylamminopropyl-carbamoyl)-ergoline and 3.1 ml of ethylisocyanate are added sequentially to a solution of 0.13 g of CuCl and 0.34 g of PPh$_3$ in 200 ml of CH$_2$Cl$_2$, in an Argon atmosphere and are stirred at 35° C. for 15 hrs. The solvent is then removed from the reaction mixture and the residue is applied to a chromatographic column packed with 50 g of kieselgel (0.05–0.2 mm) and eluted with acetone. Eluate fractions containing the product were evaporated under reduced pressure and then purified by cristallization to give 3.95 g of the title compound.

EXAMPLE 2

6-Allyl-8β-[1-ethyl-3-(3-dimethylamminopropyl)-ureidocarbonyl]-ergoline (I: $R_1=C_2H_5$, $R_2=(CH_2)_3N(CH_3)_2$, $R_3=CH_2CHCH_2$)

The same as in EXAMPLE 1 but employing 0.17 g of CuCl$_2$ as catalyst, and leaving the reaction at 35° C. for 24 hrs; 3.67 g of the title compound were obtained.

EXAMPLE 3

6-Allyl-8β-[1-ethyl-3-(3-dimethylamminopropyl)-ureidocarbonyl]-ergoline (I: $R_1=C_2H_5$, $R_2=(CH_2)_3N(CH_3)_2$, $R_3=CH_2CHCH_2$)

The same as in EXAMPLE 1 but employing 200 ml of C$_2$H$_4$Cl$_2$ as solvent, and heating the reaction at 40° C. for 12 hrs; 4.32 g of the title compound were obtained.

EXAMPLE 4

6-Allyl-8β-[1-ethyl-3-(3-dimethylamminopropyl)-ureidocarbonyl]-ergoline (I: $R_1=C_2H_5$, $R_2=(CH_2)_3N(CH_3)_2$, $R_3=CH_2CHCH_2$)

The same as in EXAMPLE 1 but employing 200 ml of toluene as solvent, and heating the reaction at 60° C. for 24 hrs; 3.62 g of the title compound were obtained.

We claim:

1. A process for the preparation of an ergoline derivative of the formula I

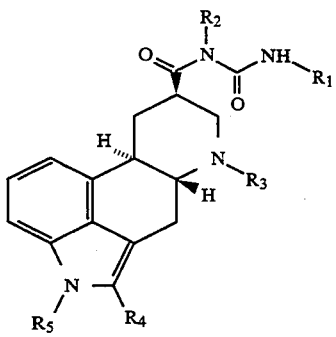

wherein $R_1$ represents an alkyl group having from 1 to 4 carbon atoms, a cyclohexyl group or a phenyl group or a dimethylamino alkyl group $(CH_2)_nN(CH_3)_2$ in which n is an integer, $R_2$ represents any of the group which $R_1$ may represent, or a hydrogen atom or a pyridyl, pyrimidyl, pyrazinyl, pyridazinyl, thiazolyl or thiadiazolyl residue, $R_3$ represents a hydrocarbon group having from 1 to 4 carbon atoms, $R_4$ represents a hydrogen or a halogen atom or a methylthio or phenylthio group and $R_5$ represents a hydrogen atom or a methyl group, the process comprising reacting an ergoline amide of the formula II with an isocyanate of formula III.

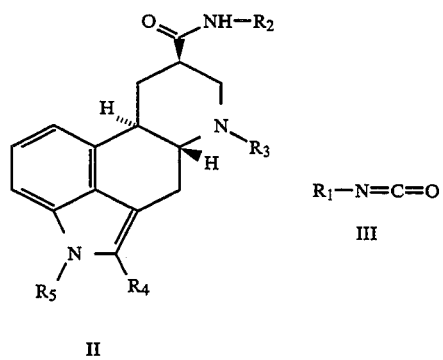

wherein $R_1$, $R_2$, $R_3$, $R_4$ and $R_5$ have the above given meanings, in presence of a metal catalyst and of a phosphorus compound.

2. A process according to claim 1 wherein the reaction is carried out in a suitable solvent at a temperature of from 0° to 80° C. and the metal catalyst is chosen from Ib and IIb metal group salts.

3. A process according to claim 2 wherein the Ib and IIb metal salt is CuCl, CuCl$_2$, CuBr or CuI.

4. A process according to any one of claims 1 to 3 wherein the phosphorus compound is a phosphine of the formula PR$_6$R$_7$R$_8$ in which R$_6$, R$_7$ and R$_8$ are each, independently, an alkyl or aryl group optionally substituted by one or more substituents chosen from Cl, F, methyl and methoxy, or is an alkyl phosphite.

5. A process according to any one of claims 1 to 3 wherein the phosphorus compound is triphenylphosphine or triparatolylphosphine.

6. A process according to any one of claims 2 to 3 wherein the solvent is dichloromethane, 1,1-dichloroethane, chloroform, toluene, acetonitrile or dimethylformamide and the reaction is carried out at a temperature of from 35° to 60° C.

7. A process according to any one of claims 1 to 3 wherein R$_1$ is an ethyl group, R$_2$ is a dimethylaminopropyl group, R$_3$ is an allyl group, R$_4$ and R$_5$ are hydrogen atoms.

8. A process according to any one of claims 1 to 3 which further comprises converting the ergoline derivative of formula (I) into a pharmaceutically acceptable salt thereof.

9. The process according to claim 4, wherein the phosphorous compound is triphenylphosphine or triparatolylphosphine.

10. The process according to claim 4, wherein the solvent is dichloromethane, 1,1-dichloroethane, chloroform, toluene, acetonitrile or dimethylformamide and the reaction is carried out at a temperature of from 35°–60° C.

11. The process according to claim 5, wherein the solvent is dichloromethane, 1,1-dichloroethane, chloroform, toluene, acetonitrile or dimethylformamide and the reaction is carried out at a temperature of from 35°–60° C.

12. The process according to claim 4, wherein $R_1$ is an ethyl group, $R_2$ is a dimethylaminopropyl group, $R_3$ is an allyl group, and $R_4$ and $R_5$ are hydrogen atoms.

13. The process according to claim 5, wherein $R_1$ is an ethyl group, $R_2$ is a dimethylaminopropyl group, $R_3$ is an allyl group, and $R_4$ and $R_5$ are hydrogen atoms.

14. The process according to claim 6, wherein $R_1$ is an ethyl group, $R_2$ is a dimethylaminopropyl group, $R_3$ is an allyl group, and $R_4$ and $R_5$ are hydrogen atoms.

15. The process according to claim 4, which further comprises converting the ergoline derivative of formula (I) into a pharmaceutically acceptable salt thereof.

16. The process according to claim 5, which further comprises converting the ergoline derivative of formula (I) into a pharmaceutically acceptable salt thereof.

17. The process according to claim 6, which further comprises converting the ergoline derivative of formula (I) into a pharmaceutically acceptable salt thereof.

18. The process according to claim 7, which further comprises converting the ergoline derivative of formula (I) into a pharmaceutically acceptable salt thereof.

* * * * *